United States Patent
Tang et al.

(10) Patent No.: US 12,412,930 B2
(45) Date of Patent: Sep. 9, 2025

(54) ELECTROLYTE AND ELECTROCHEMICAL DEVICE

(71) Applicant: NINGDE AMPEREX TECHNOLOGY LIMITED, Ningde (CN)

(72) Inventors: Chao Tang, Ningde (CN); Lilan Zhang, Ningde (CN); Junfei Liu, Ningde (CN); Jianming Zheng, Ningde (CN)

(73) Assignee: NINGDE AMPEREX TECHNOLOGY LIMITED, Ningde (CN)

( * ) Notice: Subject to any disclaimer, the term of this patent is extended or adjusted under 35 U.S.C. 154(b) by 1231 days.

(21) Appl. No.: 16/961,495

(22) PCT Filed: Dec. 26, 2019

(86) PCT No.: PCT/CN2019/128851
§ 371 (c)(1),
(2) Date: Jul. 10, 2020

(87) PCT Pub. No.: WO2021/128205
PCT Pub. Date: Jul. 1, 2021

(65) Prior Publication Data
US 2021/0408601 A1 Dec. 30, 2021

(51) Int. Cl.
*H01M 10/0568* (2010.01)
*C07C 255/05* (2006.01)
(Continued)

(52) U.S. Cl.
CPC ....... *H01M 10/0568* (2013.01); *C07C 255/05* (2013.01); *C07D 319/12* (2013.01);
(Continued)

(58) Field of Classification Search
CPC ......... H01M 10/0568; H01M 10/0567; H01M 10/0569; H01M 2300/0028
See application file for complete search history.

(56) References Cited

U.S. PATENT DOCUMENTS

| | | | | |
|---|---|---|---|---|
| 2006/0228625 A1* | 10/2006 | Kawashima | ........ | H01M 10/052 429/200 |
| 2012/0308881 A1* | 12/2012 | Tokuda | ............ | H01M 10/0567 429/199 |

(Continued)

FOREIGN PATENT DOCUMENTS

| | | |
|---|---|---|
| CN | 1398013 A | 2/2003 |
| CN | 1845372 A | 10/2006 |

(Continued)

OTHER PUBLICATIONS

European Extended Search Report mailed Sep. 5, 2023, in counterpart European application EP 19 908 073.0, 7 pages in English.

*Primary Examiner* — Helen Oi K Conley
*Assistant Examiner* — Amanda Rosenbaum
(74) *Attorney, Agent, or Firm* — XSENSUS LLP

(57) ABSTRACT

An electrolyte includes diglycolic anhydride and a trinitrile compound, with which the cycle performance and the high-temperature stability under over-discharge conditions of lithium-ion batteries are significantly improved. The electrolyte includes a compound of Formula I; and at least one of a compound of Formula II or a compound of Formula III;

$R_1$, $R_2$, $R_3$ and $R_4$ are each independently selected from hydrogen, halo, substituted or unsubstituted $C_1$-$C_{10}$ alkyl, substituted or unsubstituted $C_2$-$C_{10}$ alkenyl, substituted or unsubstituted $C_2$-$C_{10}$ alkynyl, substituted or unsubstituted $C_6$-$C_{12}$ aryl, substituted or unsubstituted $C_1$-$C_{10}$ alkoxy, or substituted or unsubstituted $C_6$-$C_{12}$ aryloxy, wherein when substituted, the substituent is halo, cyano, or $C_1$-$C_{10}$ alkyl; and a, d and f are each independently selected from an integer from 1 to 5, and b, c, e, g, h and i are each independently selected from an integer from 0 to 5.

15 Claims, No Drawings

(51) Int. Cl.
 *C07D 319/12* (2006.01)
 *H01M 10/0525* (2010.01)
 *H01M 10/0567* (2010.01)
 *H01M 10/0569* (2010.01)

(52) U.S. Cl.
 CPC ... *H01M 10/0525* (2013.01); *H01M 10/0567* (2013.01); *H01M 10/0569* (2013.01); *H01M 2300/0028* (2013.01)

(56) References Cited

U.S. PATENT DOCUMENTS

| | | | |
|---|---|---|---|
| 2013/0011728 A1* | 1/2013 | Tokuda | H01M 10/0567 429/200 |
| 2015/0162644 A1* | 6/2015 | Fujii | H01M 10/052 429/199 |
| 2019/0326640 A1 | 10/2019 | Hasegawa et al. | |
| 2021/0159539 A1 | 5/2021 | Shiraga et al. | |

FOREIGN PATENT DOCUMENTS

| | | |
|---|---|---|
| CN | 101548425 A | 9/2009 |
| CN | 101789526 A | 7/2010 |
| CN | 103492319 A | 1/2014 |
| CN | 103682416 A | 3/2014 |
| CN | 107359326 A | 11/2017 |
| CN | 107863497 A | 3/2018 |
| CN | 108023076 A | 5/2018 |
| CN | 106602141 B | 1/2019 |
| CN | 109906532 A | 6/2019 |
| CN | 110165219 A | 8/2019 |
| CN | 110313098 A | 10/2019 |
| CN | 110495043 A | 11/2019 |
| EP | 2219258 A1 | 8/2010 |
| JP | 2003031259 A | 1/2003 |
| JP | 2005050707 A | 2/2005 |
| JP | 4601273 B2 | 12/2010 |
| WO | 2018173476 A1 | 9/2018 |
| WO | 2019044238 A1 | 3/2019 |
| WO | 2019097951 A1 | 5/2019 |
| WO | 2019202835 A1 | 10/2019 |

\* cited by examiner

ELECTROLYTE AND ELECTROCHEMICAL DEVICE

CROSS REFERENCE

The present application is a National Stage application of PCT international application: PCT/CN2019/128851, filed on 26 Dec. 2019, the disclosure of which is hereby incorporated by reference in its entirety.

TECHNICAL FIELD

The present application relates to energy storage technologies, and more particularly to an electrolyte and an electrochemical device containing the electrolyte.

DESCRIPTION OF RELATED ART

Lithium-ion batteries have the advantages of high energy density, high working voltage, low self-discharge rate, long cycle life, and causing no pollution, and are widely used in computers, smart wearable devices, smart phones, unmanned aerial vehicles, electric vehicles, and other fields. With the development of modern information technology and the widened use of lithium ion batteries, more performance requirements have been put forward for lithium ion batteries in the art. For example, requirements have been put forward to increase the life of lithium-ion batteries, to prevent the batteries from bulging during continuous charge, to improve the post-cycle high-temperature resistance of the batteries, and to avoid thermal runaway of the batteries.

SUMMARY

The present application provides an electrolyte and an electrochemical device including the electrolyte. The electrolyte of the present application can significantly improve the cycling capacity retention rate of the lithium ion battery, relieve the battery expansion during the cycles, and improve the post-cycle high-temperature resistance of the battery.

In one aspect, the present application provides an electrolyte including:
  a compound of Formula I; and
  at least one of a compound of Formula II or a compound of Formula III;

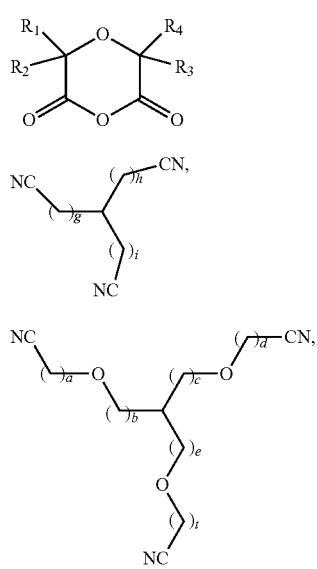

Formula I

Formula II

Formula III wherein $R_1$, $R_2$, $R_3$ and $R_4$ are each independently selected from hydrogen, halo, substituted or unsubstituted $C_1$-$C_{10}$ alkyl, substituted or unsubstituted $C_2$-$C_{10}$ alkenyl, substituted or unsubstituted $C_2$-$C_{10}$ alkynyl, substituted or unsubstituted $C_6$-$C_{12}$ aryl, substituted or unsubstituted $C_1$-$C_{10}$ alkoxy, or substituted or unsubstituted $C_6$-$C_{12}$ aryloxy, wherein when substituted, the substituent is halo, cyano, or $C_1$-$C_{10}$ alkyl; and a, d and f are each independently selected from an integer from 1 to 5, and b, c, e, g, h and i are each independently selected from an integer from 0 to 5.

According to some embodiments, in the electrolyte, the compound of Formula I includes at least one of

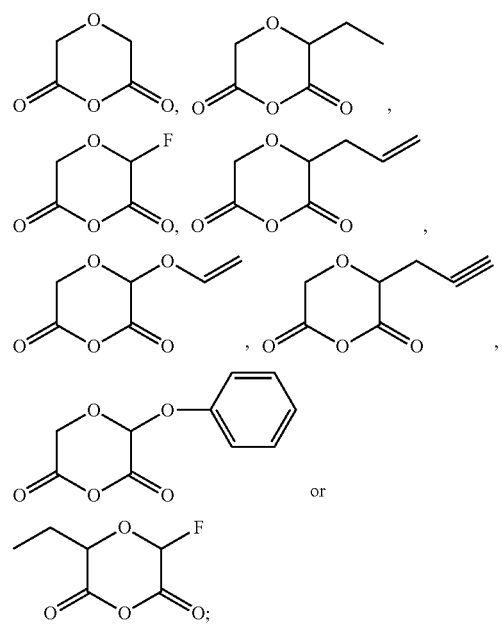

the compound of Formula II includes at least one of

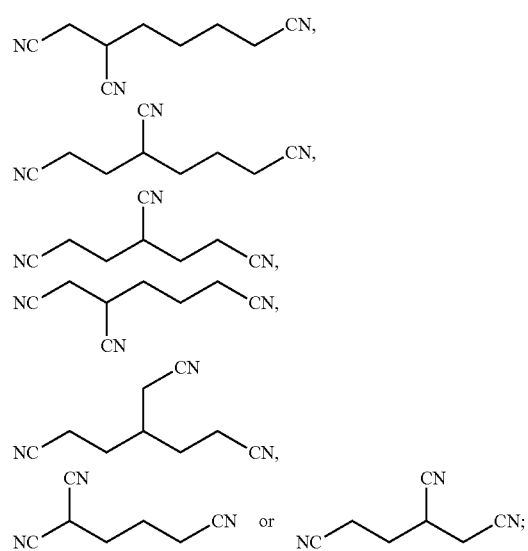

and the compound of Formula III includes at least one of

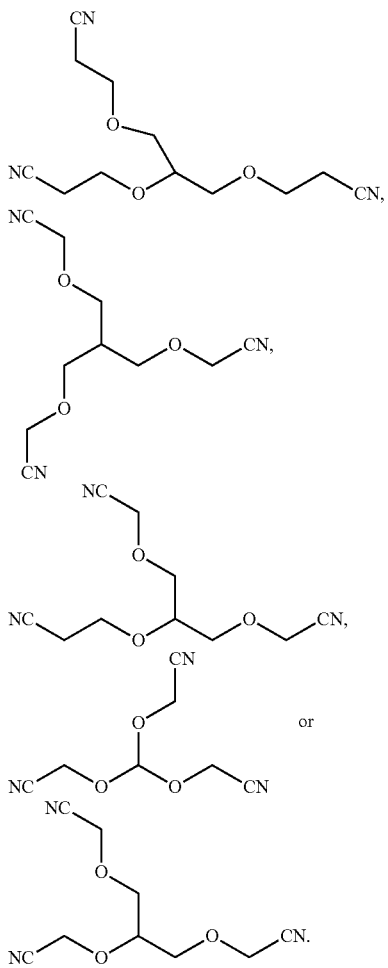

In some embodiments, the compound of Formula I accounts for about 0.01 wt % to about 3 wt % based on the weight of the electrolyte.

In some embodiments, the compound of Formula II, the compound of Formula III, or a combination thereof accounts for about 0.1 wt % to about 5 wt % based on the weight of the electrolyte.

In some embodiments, the electrolyte further includes a fluorinated additive, the fluorinated additive includes at least one of the following: fluoroethylene carbonate, a fluorinated carbonate having 2 to 7 carbon atoms, a fluorinated carboxylate having 2 to 7 carbon atoms, or a fluoroether having 2 to 7 carbon atoms.

In some embodiments, the fluorinated additive accounts for about 1 wt % to about 20 wt % based on the weight of the electrolyte.

In some embodiments, the fluorinated additive includes at least one of the following: fluorinated ethyl methyl carbonate, fluorinated dimethyl carbonate, fluorinated diethyl carbonate, fluorinated ethyl propionate, fluorinated propyl propionate, fluorinated methyl propionate, fluorinated ethyl acetate, fluorinated methyl acetate, fluorinated propyl acetate,

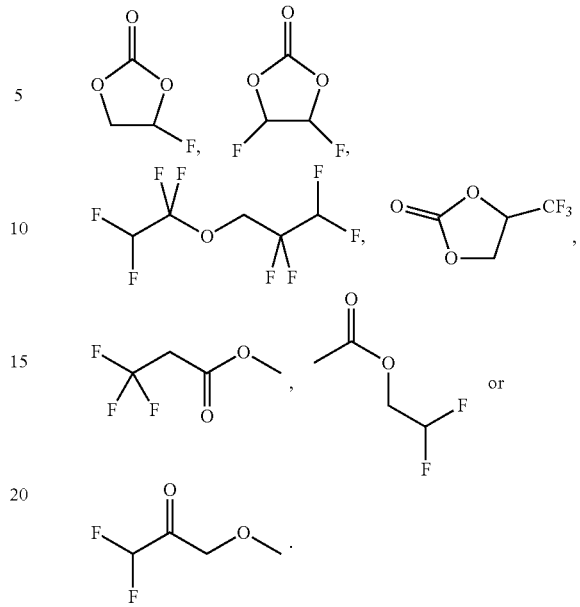

In some embodiments, the ratio of the mass fraction C of the fluorinated additive in the electrolyte to the mass fraction A of the compound of Formula I in the electrolyte is: about $1 \leq C/A \leq$ about 50.

In another aspect, the present application provides an electrochemical device, which includes a positive electrode, a negative electrode, and any electrolyte as described above.

In some embodiments, the negative electrode of the electrochemical device includes a silicon-containing material, which comprises a silicon compound $SiO_x$ where $0.5<x<1.5$, elemental silicon, or a mixture of thereof.

In some embodiments, the negative electrode of the electrochemical device includes carbon nanotubes. The carbon nanotubes have a tube diameter of about 1 nm to about 10 nm, and a tube length of about 1 micron to about 50 microns.

In some embodiments, the silicon-containing material has a carbon layer on the surface. The carbon layer has a thickness of about 1 nm to about 500 nm, and the carbon layer includes amorphous carbon, graphite, hard carbon, soft carbon, carbon black, acetylene black, carbon nanotubes or a combination thereof.

In some embodiments, the negative electrode of the electrochemical device includes graphite, wherein the weight ratio of the graphite to the silicon-containing material is about 95:5 to about 60:40.

In another aspect, the present application provides an electronic device including any electrochemical device as described above.

Additional aspects and advantages of the embodiments of the present application will be described or shown in the following description or interpreted by implementing the embodiments of the present application.

DETAILED DESCRIPTION

The embodiments of the present application will be described in detail below. The embodiments of the present application should not be interpreted as limitations to the protection scope of the present application. Unless otherwise expressly indicated, the following terms used herein have the meanings indicated below.

As used herein, the term "about" is used to describe and explain minor changes. When being used in combination with an event or circumstance, the term may refer to an example in which the event or circumstance occurs precisely, and an example in which the event or circumstance occurs approximately. For example, when being used in combination with a value, the term may refer to a variation range of less than or equal to ±10% of the value, for example, less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. In addition, sometimes, a quantity, a ratio, and another value are presented in a range format in the present application. It should be appreciated that such range formats are for convenience and conciseness, and should be flexibly understood as including not only values explicitly specified to range constraints, but also all individual values or sub-ranges within the ranges, like explicitly specifying each value and each sub-range.

In the detailed description and the claims, a list of items connected by the term "one or" may mean any one of the listed items. For example, if items A and B are listed, then the phrase "one of A and B" means only A or only B. In another example, if items A, B, and C are listed, then the phrase "one of A, B and C" means only A; only B; or only C. The item A may include a single component or multiple components. The item B may include a single component or multiple components. The item C may include a single component or multiple components.

In the detailed description and the claims, a list of items connected by the term "at least one of" may mean any combination of the listed items. For example, if items A and B are listed, then the phrase "at least one of A and B" or "at least one of A or B" means only A; only B; or A and B. In another example, if items A, B and C are listed, then the phrase "at least one of A, B and C" or "at least one of A, B or C" means only A; or only B; only C; A and B (excluding C); A and C (excluding B); B and C (excluding A); or all of A, B and C. The item A may include a single component or multiple components. The item B may include a single component or multiple components. The item C may include a single component or multiple components.

In the specific embodiment and the claims, in the expression with reference to the number of carbon atoms, i.e. the number after the capital letter "C", such as "$C_1$-$C_{10}$", "$C_3$-$C_{10}$" or the like, the number after "C", for example, "1", "3" or "10", indicate the number of carbon atoms in a specific functional group. That is, the functional groups may include 1-10 carbon atoms and 3-10 carbon atoms, respectively. For example, "$C_1$-$C_4$ alkyl" means an alkyl group having 1-4 carbon atoms, such as $CH_3$—, $CH_3CH_2$—, $CH_3CH_2CH_2$—, $(CH_3)_2CH$—, $CH_3CH_2CH_2CH_2$—, $CH_3CH_2CH(CH_3)$—, or $(CH_3)_3C$—.

As used herein, the term "alkyl group" is intended to be a linear saturated hydrocarbon structure having 1 to 10 carbon atoms. The alkyl group is also intended to be a branched or cyclic hydrocarbon structure having 3 to 10 carbon atoms. For example, the alkyl group may be an alkyl group having 1 to 10 carbon atoms, an alkyl group having 1 to 7 carbon atoms, or an alkyl group having 1 to 4 carbon atoms. When an alkyl group having a specific number of carbon atoms is defined, it is intended to cover all geometric isomers having the carbon number. Therefore, for example, "butyl" means n-butyl, sec-butyl, isobutyl, tert-butyl and cyclobutyl; and "propyl" includes n-propyl, isopropyl and cyclopropyl. Examples of the alkyl group include, but are not limited to, methyl, ethyl, n-propyl, isopropyl, cyclopropyl, n-butyl, isobutyl, sec-butyl, tert-butyl, cyclobutyl, n-pentyl, isoamyl, neopentyl, cyclopentyl, methylcyclopentyl, ethylcyclopentyl, n-hexyl, isohexyl, cyclohexyl, n-heptyl, octyl, cyclopropyl, cyclobutyl, norbornanyl and so on. Additionally, the alkyl group can be optionally substituted.

The term "alkenyl group" refers to a monovalent unsaturated hydrocarbon group which may be straight or branched and which has at least one and usually 1, 2 or 3 carbon-carbon double bonds. Unless otherwise defined, the alkenyl group typically contains from 2 to 10 carbon atoms, for example an alkenyl group having 2 to 7 carbon atoms, or an alkenyl group having 2 to 4 carbon atoms. Representative alkenyl groups include (for example) ethenyl, n-propenyl, iso-propenyl, n-but-2-enyl, butyl-3-enyl, n-hex-3-enyl, and the like. Additionally, the alkenyl group can be optionally substituted.

The term "alkynyl group" refers to a monovalent unsaturated hydrocarbon group which may be straight or branched and which has at least one and usually 1, 2 or 3 carbon-carbon triple bonds. Unless otherwise defined, the alkynyl group is typically an alkynyl group containing from 2 to 10, from 2 to 7, or from 2 to 4 carbon atoms. Representative alkynyl groups include (for example) ethynyl, prop-2-ynyl (n-propynyl), n-but-2-ynyl, n-hex-3-ynyl and the like. Additionally, the alkynyl group can be optionally substituted.

The term "aryl" encompasses both monocyclic and polycyclic systems. A polycyclic ring may have two or more rings where two carbons are shared by two adjacent rings (where the rings are "fused"), wherein at least one of the rings is aromatic and other rings may be for example, a cycloalkyl group, a cycloalkenyl group, an aryl group, a heterocyclyl group and/or a heteroaryl group. For example, the aryl may contain 6 to 12 or 6 to 10 carbon atoms. Representative aryl group includes (for example) phenyl, methylphenyl, propylphenyl, isopropylphenyl, benzyl and naphthalen-1-yl, naphthalen-2-yl and the like. Additionally, the aryl group can be optionally substituted.

The term "aryloxy" means an aryl group having the stated number of carbon atoms connected by an oxygen bridge, wherein the aryl group has the meaning as defined herein. Examples include, but are not limited to, phenoxy, p-methylphenoxy, p-ethylphenoxy and the like.

The term "alkoxy" refers to a group formed by an alkyl group connected to an oxygen atom, wherein the alkyl group has the meaning as defined herein. Representative examples of the alkoxy include, but are not limited to, methoxy, ethoxy, n-propoxy, isopropoxy, n-butoxy, sec-butoxy, tert-butoxy, pentyloxy, isopentyloxy or tert-pentyloxy, heptyloxy, octyloxy, isooctyloxy, nonyloxy, and decyloxy, etc.

The term "halo" encompasses F, Cl, Br or I.

When the above substituents are substituted, the substituent is selected from the group consisting of halo, and an alkyl group.

As used herein, the content of each component in the electrolyte is based on the total weight of the electrolyte.

I. Electrolyte

An embodiment of the present application provides an electrolyte, which includes diglycolic anhydride and a trinitrile or ether-trinitrile compound. The electrolyte can form a stable protective layer on the surface of the positive electrode and negative electrode, to significantly improve the cycle performance of batteries. Especially for a system where the negative electrode comprises a silicon active material, the electrolyte of the present application can make the protective layer on the negative electrode have good stability after charge and discharge cycles of batteries, so as to avoid safety accidents caused by thermal runaway of the batteries.

In some embodiments, the electrolyte includes
a compound of Formula I; and
at least one of a compound of Formula II or a compound of Formula III;

Formula I

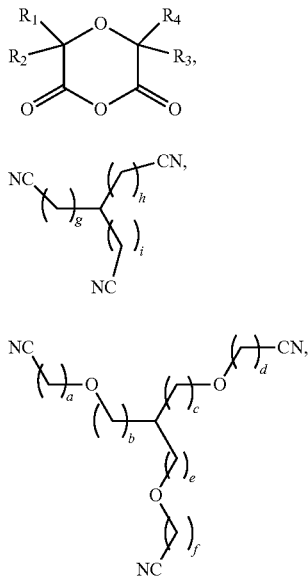

Formula II

Formula III wherein $R_1$, $R_2$, $R_3$ and $R_4$ are each independently selected from hydrogen, halo, substituted or unsubstituted $C_1$-$C_{10}$ alkyl, substituted or unsubstituted $C_2$-$C_{10}$ alkenyl, substituted or unsubstituted $C_2$-$C_{10}$ alkynyl, substituted or unsubstituted $C_6$-$C_{12}$ aryl, substituted or unsubstituted $C_1$-$C_{10}$ alkoxy, or substituted or unsubstituted $C_6$-$C_{12}$ aryloxy, wherein when substituted, the substituent is halo, cyano, or $C_1$-$C_{10}$ alkyl; and wherein a, d and f are each independently selected from an integer from 1 to 5, and b, c, e, g, h and i are each independently selected from an integer from 0 to 5.

In some embodiments, $R_1$·$R_2$·$R_3$, and $R_4$ are each independently selected from hydrogen, halo, substituted or unsubstituted $C_1$-$C_7$ alkyl, substituted or unsubstituted $C_1$-$C_4$ alkyl, substituted or unsubstituted $C_2$-$C_7$ alkenyl, substituted or unsubstituted $C_2$-$C_4$ alkenyl, substituted or unsubstituted $C_2$-$C_7$ alkynyl, substituted or unsubstituted $C_2$-$C_4$ alkynyl, substituted or unsubstituted $C_6$-$C_{10}$ aryl, substituted or unsubstituted $C_1$-$C_7$ alkoxy, substituted or unsubstituted $C_1$-$C_4$ alkoxy or substituted or unsubstituted $C_6$-$C_{10}$ aryloxy, wherein when substituted, the substituent is halo, cyano, or $C_1$-$C_3$ alkyl.

In some embodiments, $R_1$, $R_2$, $R_3$ and $R_4$ are each independently selected from H, F, methyl, ethyl, propyl, ethenyl, 1-propenyl, 2-propenyl, 1-propynyl, 2-propynyl, methoxy, ethoxy, or phenoxy.

According to some embodiments, in the electrolyte, the compound of Formula I includes at least one of

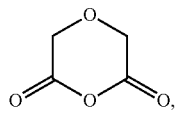
Compound 1

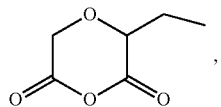
Compound 2

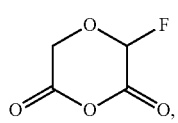
Compound 3

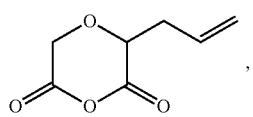
Compound 4

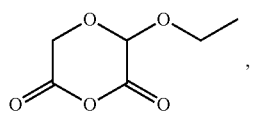
Compound 5

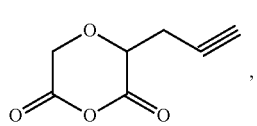
Compound 6

Compound 7

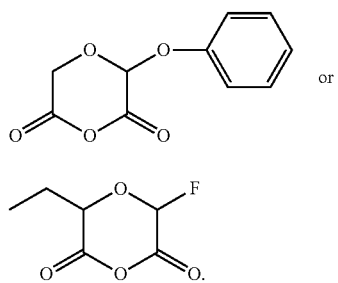
or

Compound 8

The compound of Formula II includes at least one of

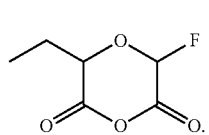
Compound 9

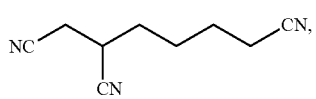
Compound 10

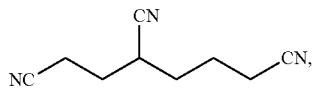
Compound 11

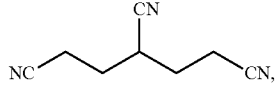
Compound 12

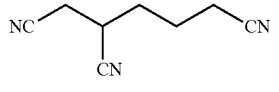

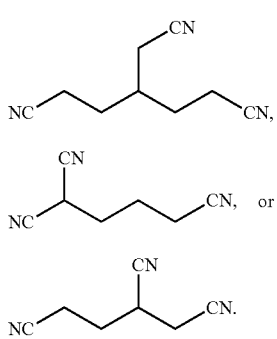

Compound 13

Compound 14

Compound 15

The compound of Formula III includes

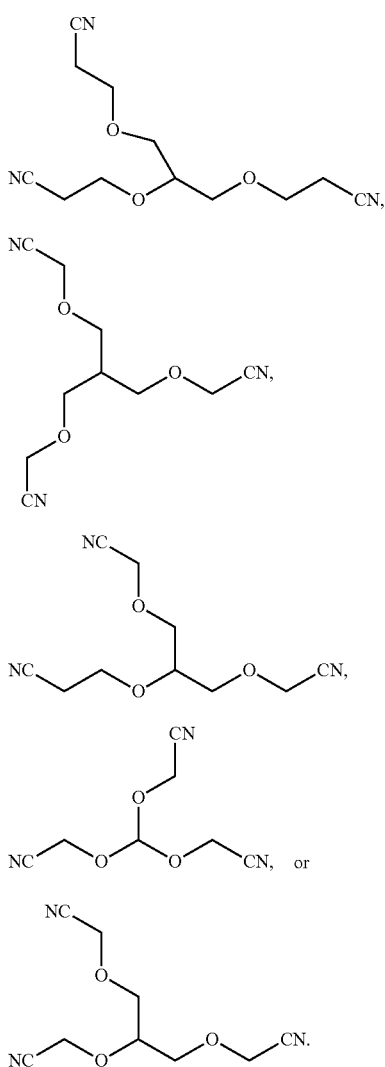

Compound 16

Compound 17

Compound 18

Compound 19

Compound 20

In some embodiments, the compound of Formula I in the electrolyte accounts for about 0.01 wt % to about 3 wt %, about 0.05 wt % to about 2 wt %, or about 0.2 wt % to about 1 wt % based on the weight of the electrolyte. In some embodiments, the compound of Formula I accounts for about 0.08 wt %, about 0.1 wt %, about 0.2 wt %, about 0.3 wt %, about 0.4 wt %, about 0.5 wt %, about 0.6 wt %, about 0.7 wt %, about 0.8 wt %, about 0.9 wt %, about 1 wt %, about 1.2 wt %, or about 1.5 wt % based on the weight of the electrolyte.

In some embodiments, the compound of Formula II, the compound of Formula III, or a combination thereof in the electrolyte accounts for about 0.1 wt % to about 5 wt %, about 0.25 wt % to about 4 wt %, about 0.5 wt % to about 3 wt %, or about 1 to about 2 wt % based on the weight of the electrolyte. In some embodiments, the compound of Formula II, the compound of Formula III, or a combination thereof in the electrolyte accounts for about 1.5 wt %, about 2 wt % or about 2.5 wt % based on the weight of the electrolyte.

In some embodiments, to further reduce the side reactions caused by the destruction of the protective layer during the cycle process of the silicon negative electrode, the electrolyte further includes a fluorinated additive, which includes at least one of the following: fluoroethylene carbonate (FEC), a fluorinated carbonate having 2 to 7 carbon atoms, a fluorinated carboxylate having 2 to 7 carbon atoms, or a fluoroether having 2 to 7 carbon atoms. Such fluorides can quickly repair the protective layer when the protective layer on the silicon negative electrode is damaged, thereby lessening side reactions of the electrolyte with the silicon negative electrode.

In some embodiments, the fluorinated additive accounts for about 1 wt % to about 20 wt % based on the weight of the electrolyte. In some embodiments, the fluorinated additive accounts for about 2 wt % to about 18 wt % based on the weight of the electrolyte. In some embodiments, the fluorinated additive accounts for about 3 wt % to about 15 wt % based on the weight of the electrolyte. In some embodiments, the fluorinated additive accounts for about 5 wt % to about 18 wt % based on the weight of the electrolyte.

In some embodiments, the fluorinated additive includes at least one of the following: fluorinated ethyl methyl carbonate, fluorinated dimethyl carbonate, fluorinated diethyl carbonate, fluorinated ethyl propionate, fluorinated propyl propionate, fluorinated methyl propionate, fluorinated ethyl acetate, fluorinated methyl acetate, or fluorinated propyl acetate.

In some embodiments, the fluorinated additive includes at least one of:

Compound 21

(FEC)

Compound 22

(DFEC)

Compound 23

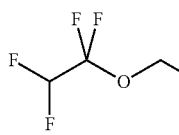

Compound 24

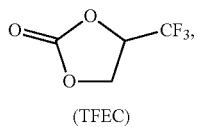

(TFEC)

Compound 25

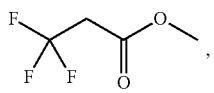

Compound 26

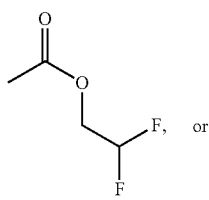
, or

Compound 27

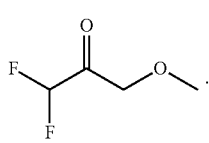
.

In some embodiments, to better form a stable protective layer and repair the protective layer, the ratio of the mass fraction C of the fluorinated additive in the electrolyte to the mass fraction A of the compound of Formula I in the electrolyte is: about 1≤C/A≤about 50.

In some embodiments, in order to further improve the cycle performance of the lithium ion battery, the electrolyte may further include at least one additive selected from vinylene carbonate (VC), 1,3-propane sultone (PS), ethylene sulfate (DTD), succinonitrile (SN) or adiponitrile (ADN).

In some embodiments, said vinylene carbonate accounts for about 0.001 wt % to about 2 wt % based on the weight of the electrolyte.

In some embodiments, said 1,3-propane sultone accounts for about 0.001 wt % to about 2 wt % based on the weight of the electrolyte. In some embodiments, 1,3-propane sultone accounts for about 0.001 wt % to about 1 wt % based on the weight of the electrolyte.

In some embodiments, ethylene sulfate accounts for about 0.001 wt % to about 3 wt % based on the weight of the electrolyte.

In some embodiments, the succinonitrile (SN), adiponitrile, or a combination thereof accounts for about 0.1 wt % to about 7 wt % based on the weight of the electrolyte.

In some embodiments, the succinonitrile (SN), adiponitrile, or a combination thereof accounts for about 0.5 wt % to about 6 wt % based on the weight of the electrolyte.

In some embodiments, the electrolyte further includes a lithium salt and an organic solvent.

In some embodiments, the lithium salt is one or more selected from the group consisting of an inorganic lithium salt and an organic lithium salt. In some embodiments, the lithium salt includes at least one of a fluorine element, a boron element, or a phosphorus element. In some embodiments, the lithium salt is one or more selected from the group consisting of lithium hexafluorophosphate (LiPF$_6$), lithium bis(trifluoromethanesulphonyl)imide (LiN(CF$_3$SO$_2$)$_2$) (LiTFSI), lithium bis(fluorosulfonyl)imide (Li(N(SO$_2$F)$_2$)(LiFSI), lithium bis(oxalato)borate (LiB(C$_2$O$_4$)$_2$) (LiBOB), lithium difluoro(oxalato)borate (LiBF$_2$(C$_2$O$_4$) (LiDFOB), lithium hexafluoroarsenate (LiAsF$_6$), lithium perchlorate (LiClO$_4$), and lithium trifluoromethanesulfonate (LiCF$_3$SO$_3$).

In some embodiments, the content of the lithium salt is about 0.5 mol/L to about 1.8 mol/L. In some embodiments, the content of the lithium salt is about 0.8 mol/L to about 1.5 mol/L. In some embodiments, the content of the lithium salt is about 0.8 mol/L to about 1 mol/L.

The organic solvent includes a cyclic ester and a chain ester. The cyclic ester is at least one selected from ethylene carbonate (EC), propylene carbonate (PC), γ-butyrolactone (BL), and butylene carbonate. The chain ester is at least one selected from the group consisting of dimethyl carbonate (DMC), diethyl carbonate (DEC), ethyl methyl carbonate (EMC), propyl ethyl carbonate, methyl formate (MF), ethyl formate (MA), ethyl acetate (EA), ethyl propionate (EP), propyl propionate (PP), methyl propionate, methyl butyrate, and ethyl butyrate.

In some embodiments, the organic solvent accounts for about 70 wt % to about 90 wt % based on the weight of the electrolyte.

II. Electrochemical Device

The electrochemical device of the present application includes any device where an electrochemical reaction takes place, and specific examples include all kinds of primary batteries, secondary batteries, fuel cells, solar cells, or capacitors. In particular, the electrochemical device is a lithium secondary battery including a lithium metal secondary battery, a lithium ion secondary battery, a lithium polymer secondary battery or a lithium ion polymer secondary battery. In some embodiments, the electrochemical device of the present application is an electrochemical device having a positive electrode having a positive electrode active material capable of absorbing and releasing metal ions; a negative electrode having a negative electrode active material capable of absorbing and releasing metal ions, and characterized by comprising any electrolyte of the present application.

Negative Electrode

The material used in the negative electrode of the electrochemical device of the present application, and the construction and manufacturing methods therefor are not particularly limited, and may be any of the techniques disclosed in the prior art. In some embodiments, the negative electrode may be one described in U.S. Pat. No. 9,812,739B, which is incorporated herein by reference in its entirety.

In some embodiments, the negative electrode includes a current collector and a negative electrode active material layer on the current collector. The negative electrode active material includes a material that reversibly intercalates/deintercalates lithium ions. In some embodiments, the material that reversibly intercalates/deintercalates lithium ions includes a carbon material. In some embodiments, the carbon material may be any carbon-based negative electrode active material commonly used in lithium ion rechargeable batteries. In some embodiments, the carbon material includes, but is not limited to, crystalline carbon, amorphous carbon, or a mixture thereof. The crystalline carbon may be formless or plate-shaped, platelet-shaped, spherical or fibrous natural graphite or artificial graphite. The amorphous carbon may be soft carbon, hard carbon, carbonized mesophase pitch, calcined coke, and the like.

In some embodiments, the negative electrode active material layer includes a negative electrode active material. The negative electrode active material includes at least one of a carbon-containing material, a silicon-containing material, an alloy material, or a tin-containing material. In some embodiments, the negative electrode active material includes, but is not limited to, lithium metal, structured lithium metal, natural graphite, artificial graphite, mesocarbon microbead (MCMB), hard carbon, soft carbon, silicon, silicon-carbon composite, Li—Sn alloy, Li—Sn—O alloy, Sn, SnO, $SnO_2$, lithiated $TiO_2$—$Li_4Ti_5O_{12}$ having spinel structure, Li—Al alloy and any combination thereof.

In some embodiments, the negative electrode active material includes a silicon-containing material, the silicon-containing material includes a silicon compound $SiO_x$ where $0.5 \leq x \leq 1.5$, elemental silicon, or a mixture of thereof.

In some embodiments, the mass fraction of the silicon-containing material is about 5 wt % to about 90 wt %, about 10 wt % to about 70 wt %, or about 10 wt % to about 50 wt % based on the total weight of the negative electrode active material.

In some embodiments, to further improve the conductivity of the silicon-containing material, the silicon-containing material has a carbon layer on its surface to promote the formation of a stable protective layer on the surface of the negative electrode by the additive diglycolic anhydride. The carbon layer may be at least one selected from amorphous carbon, graphite, hard carbon, soft carbon, carbon black, acetylene black or carbon nanotubes. The thickness of the carbon layer is about 1 nm to about 500 nm, about 10 nm to about 300 nm, or about 20 nm to about 200 nm.

In some embodiments, when the negative electrode comprises a silicon-containing material, the negative electrode may further include a carbon nanotube conductive agent, to avoid failure in electrical contact caused by the expansion and contraction of the silicon negative electrode during charge and discharge processes, and improve cycling capacity retention rate and post-cycle thermal safety of secondary batteries with a silicon negative electrode. In some embodiments, the carbon nanotube has a tube diameter of about 1 nm to about 10 nm and a tube length of about 1 nm to about 50 μm. The carbon nanotube is in close contact with the silicon surface or the coating on the surface of silicon.

In some embodiments, the negative electrode active material layer includes a binder, and optionally a conductive material. The binder increases the binding of negative electrode active material particles and the binding of the negative electrode active material to the current collector. In some embodiments, the binder includes, but is not limited to, polyvinyl alcohol, carboxymethyl cellulose, hydroxypropyl cellulose, diacetyl cellulose, polyvinyl chloride, carboxylated polyvinyl chloride, polyvinyl fluoride, a polymer containing ethylene oxide, polyvinylpyrrolidone, polyurethane, polytetrafluoroethylene, poly(1,1-vinylidene fluoride), polyethylene, polypropylene, styrene butadiene rubber, acrylated styrene butadiene rubber, epoxy resins, Nylon and so on.

In some embodiments, the conductive material includes, but is not limited to, a carbon based material, a metal based material, a conductive polymer, or a mixture thereof. In some embodiments, the carbon-based material is selected from natural graphite, artificial graphite, carbon black, acetylene black, ketjen black, carbon fiber, or any combinations thereof. In some embodiments, the metal based material is selected from metal powders, metal fibers, copper, nickel, aluminum, and silver. In some embodiments, the conductive polymer is a polyphenylene derivative.

In some embodiments, the negative electrode current collector includes, but is not limited to, copper foil, nickel foil, stainless steel foil, titanium foil, foamed nickel, foamed copper, polymeric substrates coated with a conductive metal, and any combinations thereof.

The negative electrode can be produced by a production method well known in the art. For example, the negative electrode can be obtained by mixing an active material, a conductive material and a binder in a solvent to prepare an active material composition, and coating the active material composition on a current collector. In some embodiments, the solvent may include, but is not limited to, water.

Positive Electrode

The material used in positive electrode of the electrochemical device of the present application can be prepared using materials, construction and manufacturing methods well known in the art. In some embodiments, the positive electrode of the present application can be prepared using the technique described in U.S. Pat. No. 9,812,739B, which is incorporated herein by reference in its entirety.

In some embodiments, the positive electrode includes a current collector and a positive electrode active material layer on the current collector. The positive electrode active material includes at least one lithiated intercalation compound that reversibly intercalates and deintercalates lithium ions. In some embodiments, the positive electrode active material includes a composite oxide. In some embodiments, the composite oxide contains lithium and at least one element selected from the group consisting of cobalt, manganese, and nickel.

In some embodiments, the positive electrode active material is one or more selected from lithium cobalt oxide, lithium manganese oxide, lithium nickel oxide, or a lithium nickel manganese cobalt ternary material.

In some embodiments, the positive electrode active material may have a coating on its surface or may be mixed with another compound having a coating. The coating may include at least one coating element compound selected from the group consisting of an oxide of a coating element, a hydroxide of a coating element, an oxyhydroxide of a coating element, an oxycarbonate of a coating element, and a hydroxycarbonate of a coating element. The compound used for the coating may be amorphous or crystalline.

In some embodiments, the coating element contained in the coating may include Mg, Al, Co, K, Na, Ca, Si, Ti, V, Sn, Ge, Ga, B, As, Zr or any combinations thereof. The coating can be applied by any method as long as the method does not adversely affect the performance of the positive electrode active material. For example, the method may include any coating method known in the art, such as spraying, dipping, and others.

The positive electrode active material layer further includes a binder, and optionally a conductive material. The binder increases the binding of the positive electrode active material particles to each other and the binding of the positive electrode active material to the current collector.

In some embodiments, the binder includes, but is not limited to, polyvinyl alcohol, hydroxypropyl cellulose, diacetyl cellulose, polyvinyl chloride, carboxylated polyvinyl chloride, polyvinyl fluoride, a polymer containing ethylene oxide, polyvinylpyrrolidone, polyurethane, polytetrafluoroethylene, poly(1,1-vinylidene fluoride), polyethylene, polypropylene, styrene butadiene rubber, acrylated styrene butadiene rubber, epoxy resins, Nylon and so on.

In some embodiments, the conductive material includes, but is not limited to, a carbon based material, a metal based material, a conductive polymer, and a mixture thereof. In some embodiments, the carbon-based material is selected from natural graphite, artificial graphite, carbon black, acetylene black, ketjen black, carbon fiber, carbon nanotubes, graphene or any combinations thereof. In some embodiments, the metal based material is selected from the group consisting of metal powders, metal fibers, copper, nickel, aluminum, and silver. In some embodiments, the conductive polymer is a polyphenylene derivative.

In some embodiments, the positive electrode current collector may be, but is not limited to, aluminum.

The positive electrode can be prepared by a preparation method well known in the art. For example, the positive electrode can be obtained by mixing an active material, a conductive material and a binder in a solvent to prepare an active material composition, and coating the active material composition on a current collector. In some embodiments, the solvent may include, but is not limited to, N-methylpyrrolidone or the like.

In some embodiments, the positive electrode is prepared by forming a positive electrode material with a positive electrode active material layer including a lithium-transition metal compound powder and a binder on a current collector.

In some embodiments, the positive electrode active material layer can generally be produced by dry mixing a positive electrode material and a binder (and a conductive material and a thickener if needed) to form flakes, and pressing the obtained flakes on a positive electrode current collector; or dissolving or dispersing the material in a liquid medium to form a slurry, coating the slurry on a positive electrode current collector, and drying. In some embodiments, the material of the positive electrode active material layer includes any material known in the art.

Separator Film

In some embodiments, the electrochemical device of the present application is provided with a separator film between the positive electrode and the negative electrode to prevent short circuit. The material and shape of the separator film used in the electrochemical device of the present application are not particularly limited, and may be any of the techniques disclosed in the prior art. In some embodiments, the separator film includes a polymer or an inorganic substance or the like formed of a material which is stable against the electrolyte of the present application.

For example, the separator film may include a substrate layer and a surface treatment layer. The substrate layer is a non-woven fabric, film, or composite film having a porous structure, and the material of the substrate layer is at least one selected from the group consisting of polyethylene, polypropylene, polyethylene terephthalate, and polyimide. Particularly, a porous polypropylene film, a porous polyethylene film, a polypropylene nonwoven fabric, a polyethylene nonwoven fabric, and a porous polypropylene-polyethylene-polypropylene composite film may be used. One or more substrate layers may be present. When more than one substrate layers are present, the polymers in different substrate layers may have the same or different composition(s), and the weight average molecular weights of the polymers in different substrate layers are not exactly the same. When more than one substrate layers are present, the shutdown temperature of the polymers in different substrate layers is different.

In some embodiments, at least one surface of the substrate layer is provided with a surface treatment layer, which may be a polymer layer or an inorganic layer, or a layer formed by mixing a polymer and an inorganic material.

The inorganic layer includes inorganic particles and a binder. The inorganic particles are at least one selected from the group consisting of alumina, silica, magnesia, titania, hafnium dioxide, tin oxide, cerium dioxide, nickel oxide, zinc oxide, calcium oxide, zirconia, yttria, silicon carbide, eboehmite, aluminum hydroxide, magnesium hydroxide, calcium hydroxide and barium sulfate, or a combination of more than one thereof. The binder is one selected from the group consisting of polyvinylidene fluoride, a copolymer of vinylidene fluoride-hexafluoropropylene, a polyamide, polyacrylonitrile, a polyacrylate ester, polyacrylic acid, a polyacrylate salt, polyvinylpyrrolidone, polyvinyl ether, polymethyl methacrylate, polytetrafluoroethylene, and polyhexafluoropropylene, or a combination of more than one thereof. The polymer layer contains a polymer, and the material of the polymer includes at least one of a polyamide, polyacrylonitrile, a polyacrylate ester, polyacrylic acid, a polyacrylate salt, polyvinylpyrrolidone, polyvinyl ether, polyvinylidene fluoride or poly (vinylidene fluoride-hexafluoropropylene).

III. Application

The electrolyte according to the embodiments of the present application can significantly improve the cycle performance and the high-temperature stability under overdischarge conditions of the lithium ion battery, thus being applicable to an electronic device comprising an electrochemical device.

The use of the electrochemical device according to the present application is not particularly limited, and can be used in various known applications, such as notebook computers, pen-input computers, mobile computers, e-book players, portable phones, portable fax machines, portable copiers, portable printers, head-mounted stereo headphones, video recorders, LCD TVs, portable cleaners, portable CD players, Mini discs, transceivers, electronic notebooks, calculators, memory cards, portable recorders, radios, backup power sources, motors, vehicles, motorcycles, scooters, bicycles, lighting apparatus, toys, game consoles, clocks, electric tools, flashing light, cameras, large batteries for household use, or lithium ion capacitors.

EXAMPLES

Hereinafter, the present application will be specifically described by way of examples and comparative examples; however, the present application is not limited thereto as long as they do not deviate from the spirit of the present application.

1. Preparation of Lithium-Ion Battery (1) Preparation of Negative Electrode:

1.2 kg of 1.5 wt % carboxymethyl cellulose sodium (CMC) solution, 0.07 kg of 50 wt % styrene-butadiene rubber emulsion, 2.0 kg of graphite powder, 0.01 kg of carbon nanotubes (with a tube diameter of about 1 nm to 5 nm, and a tube length of about 1 micron to 30 microns), and 0.4 kg of SiO coated with amorphous carbon on the surface were weighed. The thickness of the amorphous carbon coating is as shown in Table 1. The materials were folly mixed and stirred to obtain a negative electrode slurry. The negative electrode slurry was then evenly coated on a copper foil with a thickness of 8 microns, baked at 120° C. for 1 hour, compacted and cut to obtain the negative electrode.

(2) Preparation of Positive Electrode:

1.42 kg of N-methyl-2-pyrrolidone (nano P), 1.2 kg of polyvinylidene fluoride (PVDF) with a mass fraction of 10%, 0.16 kg of conductive graphite and 7.2 kg of lithium cobalt oxide ($LiCoO_2$) were weighed, fully mixed and stirred, to obtain a positive electrode slurry. The positive electrode slurry was evenly coated on an aluminum foil with a thickness of 10 microns, baked at 120° C. for 1 hour, compacted and cut to obtain the positive electrode.

(3) Preparation of Electrolyte

In a glove box under a dry argon atmosphere, ethylene carbonate (EC), propylene carbonate (PC) and diethyl carbonate (DEC) were thoroughly mixed at a weight ratio of 20:10:70, and then the lithium salt $LiPF_6$ was added. Specific types and amounts of materials were added to the electrolyte (wherein the types and amounts of the added materials are shown in Table 1, and the content of each material was calculated based on the total weight of the electrolyte), and folly mixed to obtain the electrolyte. The concentration of $LiPF_6$ in the electrolyte was 1.05 mol/L.

(4) Preparation of Separator Film

A 7 micron-thick polyethylene (PE) separator film was used.

(5) Preparation of Lithium-Ion Battery

The positive electrode, the separator film and the negative electrode were positioned in order such that the separator film was placed between the positive electrode and the negative electrode to separate them. It was wound and the electrode lugs were weld to obtain an electrode assembly. The electrode assembly was placed in a packaging foil and dried. The electrolyte prepared above was injected. After vacuum packaging, standing, formation (by charging to 3.3V at a constant current of 0.02C, and then to 3.6V at a constant current of 0.1C), venting and capacity test, a lithium-ion battery was obtained.

Examples 1 to 21, and Comparative Examples 1 and 2

The electrolytes and lithium ion batteries of Examples 1-21 and Comparative Examples 1-2 were prepared following the methods as described in (1) to (5).

Example 22

The electrolyte and lithium-ion battery of Example 22 were prepared, wherein the negative electrode was prepared following the method described below, and the others were prepared according to the methods as described in (2) to (5).

1.2 kg of 1.5 wt % carboxymethyl cellulose sodium (CMC) solution, 0.07 kg of 50 wt % styrene-butadiene rubber emulsion, 2.0 kg of graphite powder, 0.01 kg of carbon nanotubes (with a tube diameter of about 1 nm to 5 nm, and a tube length of about 1 micron to 30 microns), and 0.4 kg of SiO coated with carbon nanotubes (with a tube diameter of about 1 to 5 nm, and a tube length of about 1 to 30 microns) on the surface were weighed. The thickness of the carbon nanotube coating is shown in Table 1. The materials were fully mixed and stirred to obtain a negative electrode slurry. The negative electrode slurry was then evenly coated on a copper foil with a thickness of 8 microns, baked at 120° C. for 1 h, compacted and cut to obtain the negative electrode.

Example 23

The electrolyte and lithium-ion battery of Example 23 were prepared, wherein the negative electrode was prepared following the method described below, and the others were prepared according to the methods as described in (2) to (5).

1.2 kg of 1.5 wt % carboxymethyl cellulose sodium (CMC) solution, 0.07 kg of 50 wt % styrene-butadiene rubber emulsion, 2.0 kg of graphite powder, 0.01 kg of carbon nanotubes (with a tube diameter of about 1 to 5 nm, and a tube length of about 1 to 30 microns), and 0.4 kg of SiO were weighed. The materials were fully mixed and stirred to obtain a negative electrode slurry. The negative electrode slurry was then evenly coated on a copper foil with a thickness of 8 microns, baked at 120° C. for 1 h, compacted and cut to obtain the negative electrode.

Example 24

The electrolyte and lithium-ion battery of Example 24 were prepared, wherein the negative electrode was prepared following the method described below, and the others were prepared according to the methods as described in (2) to (5).

1.2 kg of 1.5 wt % carboxymethyl cellulose sodium (CMC) solution, 0.07 kg of 50 wt % styrene-butadiene rubber emulsion, 2.0 kg of graphite powder, and 0.4 kg of SiO coated to with amorphous carbon on the surface were weighed. The thickness of the amorphous carbon coating is shown in Table 1. The materials were fully mixed and stirred to obtain a negative electrode slurry. The negative electrode slurry was then evenly coated on a copper foil with a thickness of 8 microns, baked at 120° C. for 1 h, compacted and cut to obtain the negative electrode.

Example 25

The electrolyte and lithium-ion battery of Example 25 were prepared, wherein the negative electrode was prepared following the method described below, and the others were prepared according to the methods as described in (2) to (5).

1.2 kg of 1.5 wt % carboxymethyl cellulose sodium (CMC) solution, 0.07 kg of 50 wt % styrene-butadiene rubber emulsion, and 2.4 kg of graphite powder were weighed. The materials were fully mixed and stirred to obtain a negative electrode slurry. The negative electrode slurry was then evenly coated on a copper foil with a thickness of 8 microns, baked at 120° C. for 1 hour, compacted and cut to obtain the negative electrode.

TABLE 1

| | Batteries in examples and comparative examples | | | | | |
|---|---|---|---|---|---|---|
| | Additive (wt %) | | | | | |
| | Compound of Formula I | | | | | |
| | Diglycolic anhydride | | | | Compound of Formula II and/or Formula III | |
| Examples | Compound 1 | Compound 2 | Compound 3 | Compound 5 | Compound 10 | Compound 16 |
| Comparative Example 1 | / | / | / | / | 1 | / |

TABLE 1-continued

Batteries in examples and comparative examples

| Examples | | | | | | |
|---|---|---|---|---|---|---|
| Comparative Example 2 | 0.5 | / | / | / | / | / |
| Example 1 | 0.5 | / | / | / | 1 | / |
| Example 2 | 0.2 | / | / | / | 1 | / |
| Example 3 | 1 | / | / | / | 1 | / |
| Example 4 | 2 | / | / | / | 1 | / |
| Example 5 | 3 | / | / | / | 1 | / |
| Example 6 | 0.5 | / | / | / | 0.5 | / |
| Example 7 | 0.5 | / | / | / | 2 | / |
| Example 8 | 0.5 | / | / | / | 3 | / |
| Example 9 | 0.5 | / | / | / | 5 | / |
| Example 10 | 0.5 | / | / | / | / | 1 |
| Example 11 | / | 0.5 | / | / | 1 | / |
| Example 12 | / | / | 0.5 | / | 1 | / |
| Example 13 | / | / | / | 0.5 | 1 | / |
| Example 14 | 0.5 | / | / | / | 1 | / |
| Example 15 | 0.5 | / | / | / | 1 | / |
| Example 16 | 0.5 | / | / | / | 1 | / |
| Example 17 | 0.5 | / | / | / | 1 | / |
| Example 18 | 0.5 | / | / | / | 1 | / |
| Example 19 | 0.5 | / | / | / | 1 | / |
| Example 20 | 0.5 | / | / | / | 1 | / |
| Example 21 | 0.5 | / | / | / | 1 | / |
| Example 22 | 0.5 | / | / | / | 1 | / |
| Example 23 | 0.5 | / | / | / | 1 | / |
| Example 24 | 0.5 | / | / | / | 1 | / |
| Example 25 | 0.5 | / | / | / | 1 | / |

| Examples | Additive (wt %) Others | | Coating material on Si—O negative electrode | Thickness of coating, nm | Whether conductive carbon nanotubes are contained in the negative electrode |
|---|---|---|---|---|---|
| | Compound 21 | Compound 23 | | | |
| Comparative Example 1 | 6 | / | Amorphous carbon | 50 | Y |
| Comparative Example 2 | 6 | / | Amorphous carbon | 50 | Y |
| Example 1 | 6 | / | Amorphous carbon | 50 | Y |
| Example 2 | 6 | / | Amorphous carbon | 50 | Y |
| Example 3 | 6 | / | Amorphous carbon | 50 | Y |
| Example 4 | 6 | / | Amorphous carbon | 50 | Y |
| Example 5 | 6 | / | Amorphous carbon | 50 | Y |
| Example 6 | 6 | / | Amorphous carbon | 50 | Y |
| Example 7 | 6 | / | Amorphous carbon | 50 | Y |
| Example 8 | 6 | / | Amorphous carbon | 50 | Y |
| Example 9 | 6 | / | Amorphous carbon | 50 | Y |
| Example 10 | 6 | / | Amorphous carbon | 50 | Y |
| Example 11 | 6 | / | Amorphous carbon | 50 | Y |
| Example 12 | 6 | / | Amorphous carbon | 50 | Y |
| Example 13 | 6 | / | Amorphous carbon | 50 | Y |
| Example 14 | / | 6 | Amorphous carbon | 50 | Y |
| Example 15 | / | 10 | Amorphous carbon | 50 | Y |
| Example 16 | / | 15 | Amorphous carbon | 50 | Y |
| Example 17 | 3 | 3 | Amorphous carbon | 50 | Y |

TABLE 1-continued

| Batteries in examples and comparative examples | | | | | |
|---|---|---|---|---|---|
| Example 18 | 6 | / | Amorphous carbon | 20 | Y |
| Example 19 | 6 | / | Amorphous carbon | 100 | Y |
| Example 20 | 6 | / | Amorphous carbon | 200 | Y |
| Example 21 | 6 | / | Amorphous carbon | 500 | Y |
| Example 22 | 6 | / | Carbon nanotube | 50 | Y |
| Example 23 | 6 | / | Without coating layer | 0 | Y |
| Example 24 | 6 | / | Amorphous carbon | 50 | N |
| Example 25 | 6 | / | The negative electrode active material is exclusively graphite | / | / |

Note:
"/" means not present

2. Cycle Performance Test of Lithium-Ion Battery (1) Cycle Performance Test of Lithium-Ion Battery At 25° C., the lithium-ion battery was allowed to stand for 30 minutes, then charged to a voltage of 4.45V at a constant current of 0.5C and then charged at a constant voltage of 4.45V until the current is 0.05C, allowed to stand for 5 minutes, and then discharged to a voltage of 3.0V at a constant current of 0.5C. This was one charge-discharge cycle, and the corresponding discharge capacity was the first discharge capacity of the lithium ion battery. The lithium ion battery was amenable to 500 charge-and-discharge cycles as described above, and the discharge capacity at the $N^{th}$ cycle was detected. For each example 5 batteries were tested.

Capacity retention rate (%) of lithium-ion battery after $N$ cycles=discharge capacity of the $N^{th}$ cycle/the first discharge capacity×100%.

(2) Post-Cycle High-Temperature Resistance Test of Lithium-Ion Batteries Upon Over Discharge After the cycles, the capacity retention rate of the battery declined to 70%. The battery was placed in an oven, and heated at room temperature at a ramping rate of 2° C./minute until the battery burned and failed. The temperatures in the oven and at the surface of the battery were monitored, and the failure temperature of the battery was recorded. For each example 5 batteries were tested.

(3) Energy Density Test of Batteries

Battery size test: Three batteries from Example 1 and Example 24 were taken, charged to 3.9V at 25° C. at a constant current of 0.5C, and then charged at a constant voltage to 0.05C. The battery thickness, width, and length were measured use a micrometer.

At 25° C., the battery was charged to 4.45V at a constant current of 0.5C, and then charged at a constant voltage to 0.025C. The battery was allowed to stand for 5 minutes; and discharged to 3.0V at a constant current of 0.1C. The discharge energy of the lithium ion battery was recorded.

Energy density (Wh/L)=discharge energy (Wh)/(battery thickness (mm)×battery width (mm)×battery length (mm)×$10^{-6}$)

A. The electrolytes and lithium ion batteries of Examples 1 to 23 and Comparative Examples 1 to 2 were prepared following the methods as described above. The cycling capacity retention rates after various cycles and the post-cycle failure temperature of the lithium-inn battery were tested. The test results are shown in Table 2.

TABLE 2

Test results for cycling capacity retention rate and high temperature resistance

| Examples | Capacity retention rate after various cycles, % | | | | | Post-cycle failure temperature, ° C. |
|---|---|---|---|---|---|---|
| | After 100 cycles | After 200 cycles | After 300 cycles | After 400 cycles | After 500 cycles | |
| Comparative Example 1 | 93.70 | 88.97 | 83.60 | 73.89 | 61.67 | 138.6 |
| Comparative Example 2 | 93.36 | 87.06 | 81.74 | 70.09 | 58.93 | 131.2 |
| Example 1 | 96.48 | 93.75 | 90.27 | 85.39 | 83.08 | 158.8 |
| Example 2 | 95.52 | 92.81 | 89.37 | 84.93 | 82.25 | 153.7 |
| Example 3 | 96.58 | 93.88 | 90.46 | 85.78 | 83.16 | 160.5 |
| Example 4 | 96.00 | 93.29 | 89.81 | 85.26 | 82.46 | 162.3 |
| Example 5 | 94.78 | 91.22 | 86.34 | 80.48 | 76.82 | 162.5 |
| Example 6 | 96.38 | 93.57 | 90.04 | 84.73 | 82.39 | 156.6 |
| Example 7 | 96.43 | 93.62 | 90.12 | 84.85 | 82.84 | 163.6 |
| Example 8 | 95.66 | 92.87 | 89.40 | 83.17 | 81.18 | 165.3 |
| Example 9 | 94.99 | 91.82 | 88.48 | 81.59 | 79.61 | 168.1 |
| Example 10 | 96.53 | 93.70 | 90.43 | 85.79 | 83.15 | 157.3 |
| Example 11 | 96.29 | 93.59 | 89.39 | 84.22 | 82.54 | 158.5 |
| Example 12 | 96.35 | 93.63 | 89.66 | 84.47 | 82.82 | 158.7 |
| Example 13 | 96.16 | 93.35 | 88.59 | 83.35 | 81.88 | 157.6 |
| Example 14 | 96.39 | 93.34 | 89.84 | 84.93 | 81.60 | 155.4 |
| Example 15 | 96.03 | 92.68 | 88.78 | 83.68 | 80.29 | 151.4 |
| Example 16 | 95.64 | 91.61 | 87.33 | 82.65 | 79.65 | 149.5 |
| Example 17 | 96.54 | 94.29 | 91.12 | 86.44 | 83.91 | 160.5 |
| Example 18 | 95.74 | 92.64 | 88.78 | 83.41 | 80.82 | 152.3 |
| Example 19 | 96.89 | 94.26 | 90.66 | 85.64 | 83.61 | 159.6 |
| Example 20 | 96.70 | 93.98 | 90.19 | 85.47 | 83.54 | 160.5 |
| Example 21 | 95.03 | 91.54 | 87.82 | 82.11 | 77.83 | 162.8 |
| Example 22 | 97.44 | 94.19 | 91.17 | 85.84 | 83.68 | 156.7 |
| Example 23 | 95.52 | 91.81 | 87.37 | 83.04 | 79.25 | 148.6 |
| Example 24 | 94.65 | 90.88 | 86.46 | 79.68 | 74.42 | 158.2 |
| Example 25 | 97.37 | 95.26 | 93.58 | 91.84 | 88.67 | 165.4 |

It can be known from the test results of Example 1 and Comparative Examples 1 and 2 that the addition of the compound of Formula I and the compound of Formula II or Formula III to the electrolyte can significantly improve the cycle performance, and the post-cycle high-temperature resistance and safety of lithium ion batteries with a silicon-containing negative electrode.

It can be seen from the test results of Examples 1 to 5 and Comparative Example 2 that the addition of the compound of Formula II (e.g., Compound 10) and various contents of the compound of Formula I (e.g., Compound 1) to the electrolyte can significantly improve the cycle performance, and the post-cycle high-temperature resistance and safety of lithium ion batteries with a silicon-containing negative electrode. A suitable amount of the compound of Formula I and a suitable amount of the compound of Formula II work together to achieve an excellent film-forming performance and a fast reaction rate on the surface of the silicon negative electrode. If the amount added is too high, it is easy to form a thick protective layer, which hinders the intercalation and deintercalation of lithium ions on the silicon surface, and does not seem conducive to the cycling capacity retention rate. On the other hand, the thicker the protective layer is, the better the post-cycle high-temperature resistance will be. This is because a thick protective layer can well suppress side reactions of the electrolyte on the silicon surface, and reduce the release of heat, thereby improving high-temperature resistance and safety. Considering the above factors, the desired effect can be achieved when the compound of Formula I added accounts for about 0.5 to about 2 wt % of electrolyte.

According to the test results of Example 1 and Examples 11 to 13, it can be seen that when each example of the compound of Formula I (e.g., Compound 1, 2, 3, or 5) and the compound of Formula II (e.g., Compound 10) are added to the electrolyte in combination, similar technical effects can be obtained.

According to the test results of Example 1, Examples 6 to 9 and Comparative Example 2, it can be known that addition of a suitable amount of the compound of Formula I (e.g., Compound 1) as well as the compound of Formula II (e.g., Compound 10) in the range of about 0.1 to about 5 wt % to the electrolyte can significantly improve the capacity retention rate and the post-cycle thermal safety of the lithium ion battery; particularly, the post-cycle high-temperature resistance of the battery is significantly improved. When the battery contains no trinitrile or ether-trinitrile additives, the post-cycle high-temperature resistance and safety of the batteries is significantly reduced. In view of the above factors, when the amount of the compound of Formula II added is about 0.5 wt % to about 3 wt %, the effect is particularly desirable.

According to the test results of Example 1 and Example 10, it can be seen that the combination of the compound of Formula II (e.g. Compound 10) or the compound of Formula III (e.g. Compound 16) with the compound of Formula I (e.g. Compound 1) has a similar improvement effect.

According to the test results of Example 1 and Example 17, it can be seen that addition of an appropriate amount of a fluorinated additive (e.g. the combination of Compound 23 and Compound 21) to the electrolyte can further improve the cycle performance and the post-cycle high-temperature resistance of the lithium ion battery with a silicon-containing negative electrode.

It can be seen through comparison of test results of Examples 1 and 18 to 22 with Example 23 that the electrolyte of the present application is applicable to lithium-ion batteries having an negative electrode made of a silicon negative electrode material coated with amorphous carbon or carbon nanotubes, and is also applicable to lithium ion batteries having an negative electrode made of a silicon negative electrode material without a coating; and the former has improved cycle performance and post-cycle high-temperature resistance compared with the latter. This may be attributed to the fact that the conductivity of the silicon negative electrode material is poor, after its surface is coated with a conductive coating layer, the uniformity in film formation of the protective layer is improved, thereby reducing the occurrence of side reactions of the electrolyte on the surface of the silicon negative electrode, and improving the cycle performance and the post-cycle high-temperature resistance of lithium ion batteries. According to the test results, the thickness of the carbon layer is preferably about 20 nm to about 200 nm.

This may be because the carbon material is reactive and consumes reactive lithium. When the coating layer is too thick, it will cause more loss of reactive lithium, thereby decreasing the cycling capacity retention rate.

It can be seen through comparison of test results of Example 1 and Example 24 that adding carbon nanotube conductive agent to the silicon negative electrode material and coating amorphous carbon can improve the cycle performance of silicon-containing lithium-ion batteries. This may be attributed to the fact that during the cycling process, large expansion and contraction of the silicon negative electrode occur and poor electrical contact tend to take place between particles of the negative electrode material; the addition of a long (for example, more than 1 micron) carbon nanotube conductive agent can improve electrical contact, thereby improving the cycling capacity retention rate of lithium-ion batteries.

B. The electrolytes and lithium ion batteries of Examples 1 and 25 were prepared according to the above preparation method. The energy density, cycling capacity retention rate, and high-temperature resistance of the lithium ion batteries were tested. The test results are shown in Tables 3 and 4.

TABLE 3

Energy density of batteries with various negative electrode active materials

| Examples | Battery No. | Discharge capacity Wh | Battery thickness mm | Battery width mm | Battery length mm | Energy density Wh/L |
|---|---|---|---|---|---|---|
| Example 1 | 1# | 8.307 | 3.272 | 38.914 | 95.334 | 684.32 |
| | 2# | 8.308 | 3.283 | 38.956 | 95.328 | 681.58 |
| | 3# | 8.303 | 3.283 | 39.006 | 95.312 | 680.37 |
| | Mean | 8.306 | 3.279 | 38.959 | 95.325 | 682.09 |
| Example 25 | 1# | 8.316 | 3.436 | 38.902 | 95.247 | 653.22 |
| | 2# | 8.332 | 3.447 | 38.927 | 95.331 | 651.40 |
| | 3# | 8.326 | 3.442 | 39.120 | 95.377 | 648.34 |
| | Mean | 8.325 | 3.442 | 38.983 | 95.318 | 650.99 |

TABLE 4

Test results for cycling capacity retention rate and high temperature resistance of batteries with various negative electrode active materials

| | Capacity retention rate after various cycles, % | | | | | Post-cycle failure temperature |
|---|---|---|---|---|---|---|
| Examples | After 100 cycles | After 200 cycles | After 300 cycles | After 400 cycles | After 500 cycles | |
| Example 1 | 96.48 | 93.75 | 90.27 | 85.39 | 83.08 | 158.8 |
| Example 25 | 97.37 | 95.26 | 93.58 | 91.84 | 88.67 | 165.4 |

In Example 1, a Si—O negative electrode is used, and in Example 25, a graphite negative electrode is used. The positive electrode materials in the two examples are the same. The capacity per gram of the graphite negative electrode is far lower than that of the silicon negative electrode active material. Therefore, the load of the graphite negative electrode in Example 25 is higher than that of the Si—O negative electrode in Example 1. The battery obtained in Example 25 is larger in volume and lower in energy density than Example 1.

Based on the experimental results of Example 1 and Example 25, it can be seen that both a lithium battery having a graphite negative electrode and a lithium ion battery having a Si—O negative electrode can achieve satisfactory improved capacity retention rate and post-cycle thermal safety as long as the electrolyte of the present application is used therein. The improvement for lithium batteries having a graphite negative electrode is particularly significant.

The foregoing descriptions are merely a few embodiments of the present invention and are not intended to limit the present invention in any manner. Although the present invention is described with reference to preferred embodiments, the embodiments are not intended to limit the present invention. A person skilled in the art may make some changes or modifications using the technical contents disclosed above without departing from the scope of the technical solutions of the present invention, and such changes and modifications are equivalent to equivalent implementation cases and shall fall within the scope of the technical solutions.

Throughout the specification, references to "embodiment", "part of embodiments", "one embodiment", "another example", "example", "specific example" or "part of examples" mean that at least one embodiment or example of the present application includes specific features, structures, materials or characteristics described in the embodiment or example. Thus, the descriptions appear throughout the specification, such as "in some embodiments," "in an embodiment," "in one embodiment," "in another example," "in an example," "in a particular example" or "for example," are not necessarily the same embodiment or example in the application. Furthermore, the specific features, structures, materials or characteristics in the descriptions can be combined in any suitable manner in one or more embodiments or examples.

Although the illustrative embodiments have been shown and described, it should be understood by those skilled in the art that the above embodiments cannot be interpreted as limitations to the present application, and the embodiments can be changed, substituted and modified without departing from the spirit, principle and scope of the present application.

The above-described embodiments of the present application are intended to be illustrative only. Numerous alternative embodiments may be devised by persons skilled in the art without departing from the scope of the following claims.

What is claimed is:

1. An electrolyte, consisting of:
    an organic solvent;
    a fluorinated additive;
    a compound of Formula I;
    at least one of a compound of Formula II or a compound of Formula III;

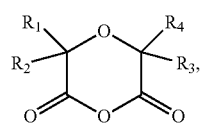

Formula I

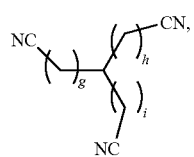

Formula II

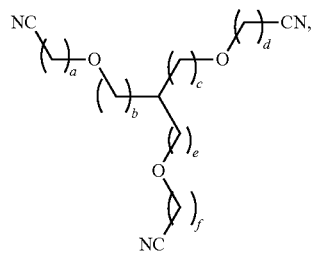

Formula III wherein $R_1$, $R_2$, $R_3$ and $R_4$ are each independently selected from hydrogen, halo, substituted or unsubstituted $C_1$-$C_{10}$ alkyl, substituted or unsubstituted $C_2$-$C_{10}$ alkenyl, substituted or unsubstituted $C_2$-$C_{10}$ alkynyl, substituted or unsubstituted $C_6$-$C_{12}$ aryl, substituted or unsubstituted $C_1$-$C_{10}$ alkoxy, or substituted or unsubstituted $C_6$-$C_{12}$ aryloxy, wherein when substituted, the substituent is halo, cyano, or $C_1$-$C_{10}$ alkyl; and a, d and f are each independently selected from an integer from 1 to 5, and b, c, e, g, h and i are each independently selected from an integer from 0 to 5;

a lithium salt; and at least one additive selected from vinylene carbonate, 1,3-propane sultone, ethylene sulfate, succinonitrile or adiponitrile, wherein the compound of Formula I is from greater than 0.01 wt % to less than or equal to 3 wt % of the weight of the electrolyte, and the compound of Formula II, the compound of Formula III, or a combination thereof is from 0.1 wt % to 5 wt % of the weight of the electrolyte; and wherein the compound of Formula I comprises at least one of:

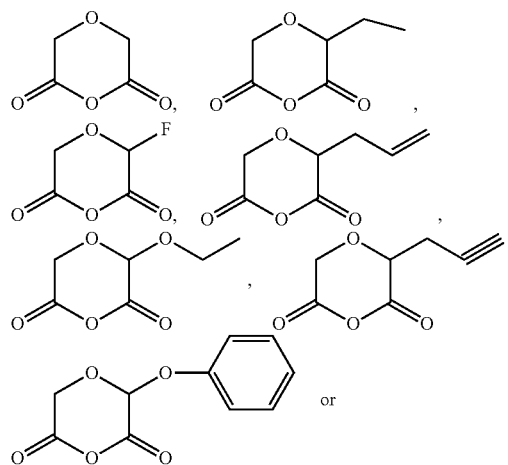

-continued

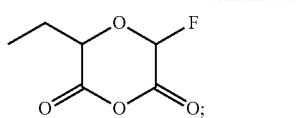

the compound of Formula II comprises at least one of

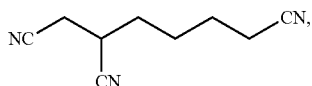

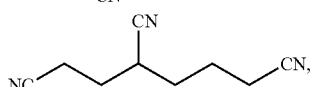

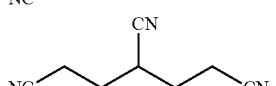

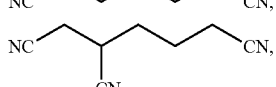

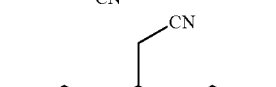

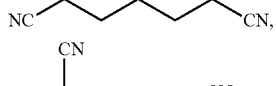

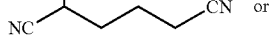

the compound of Formula III comprises at least one of

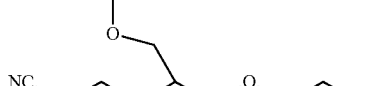

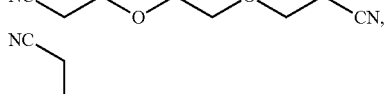

-continued

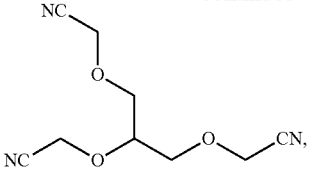

and wherein the fluorinated additive includes fluoroethylene carbonate and at least one of the following: fluorinated ethyl methyl carbonate, fluorinated dimethyl carbonate, fluorinated diethyl carbonate, fluorinated ethyl propionate, fluorinated propyl propionate, fluorinated methyl propionate, fluorinated ethyl acetate, fluorinated methyl acetate, fluorinated propyl acetate,

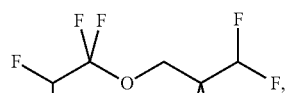

 , 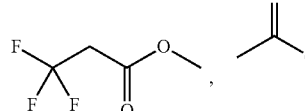 or

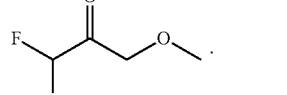

2. The electrolyte according to claim 1, wherein a ratio of the mass of the fluorinated additive (C) in the electrolyte to the mass of the compound of Formula I (A) in the electrolyte is: $1 \le C/A \le 50$.

3. An electrochemical device, comprising a positive electrode, a negative electrode, and the electrolyte according to claim 1.

4. The electrochemical device according to claim 3, wherein the negative electrode comprises a silicon-containing material, said silicon-containing material comprises a silicon compound $SiO_x$ where $0.5<x<1.5$, elemental silicon, or a mixture of thereof.

5. The electrochemical device according to claim 3, wherein the negative electrode comprises carbon nanotubes having a tube diameter of 1 nm to 10 nm, and a tube length of 1 micron to 50 microns.

6. The electrochemical device according to claim 4, wherein the silicon-containing material has a carbon layer on surface, wherein the carbon layer has a thickness of 1 nm to 500 nm, and the carbon layer includes amorphous carbon, graphite, hard carbon, soft carbon, carbon black, acetylene black, carbon nanotubes or a combination thereof.

7. The electrochemical device according to claim 3, wherein the fluorinated additive is 1 wt % to 20 wt % of the weight of the electrolyte.

8. The electrochemical device according to claim 7, wherein a ratio of the mass of the fluorinated additive (C) in the electrolyte to the mass of the compound of Formula I (A) in the electrolyte is: $1 \le C/A \le 50$.

9. The electrochemical device according to claim 7, wherein the negative electrode comprises a silicon-containing material, said silicon-containing material comprises a silicon compound $SiO_x$ where $0.5<x<1.5$, elemental silicon, or a mixture of thereof.

10. The electrochemical device according to claim 7, wherein the negative electrode comprises carbon nanotubes having a tube diameter of 1 nm to 10 nm, and a tube length of 1 micron to 50 microns.

11. The electrochemical device according to claim 9, wherein the silicon-containing material has a carbon layer on surface, wherein the carbon layer has a thickness of 1 nm to 500 nm, and the carbon layer includes amorphous carbon, graphite, hard carbon, soft carbon, carbon black, acetylene black, carbon nanotubes or a combination thereof.

12. An electronic device, comprising the electrochemical device according to claim 3.

13. The electronic device according to claim 12, wherein the fluorinated additive is 1 wt % to 20 wt % of the weight of the electrolyte.

14. The electronic device according to claim 12, wherein a ratio of the mass of the fluorinated additive (C) in the electrolyte to the mass of the compound of Formula I (A) in the electrolyte is: $1 \leq C/A \leq 50$.

15. The electronic device according to claim 12, wherein the negative electrode comprises a silicon-containing material, said silicon-containing material comprises a silicon compound $SiO_x$ where $0.5<x<1.5$, elemental silicon, or a mixture of thereof.

* * * * *